(12) United States Patent
Zhou et al.

(10) Patent No.: US 8,734,772 B1
(45) Date of Patent: May 27, 2014

(54) PHOTO-CURABLE RESIN FOR COSMETIC APPLICATION

(71) Applicant: L'Oreal, Paris (FR)

(72) Inventors: XianZhi Zhou, Leonia, NJ (US); Jean-Thierry Simonnet, Mamaroneck, NY (US); Hy Si Bui, Piscataway, NJ (US); Chunhua Li, Scotch Plains, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/729,326

(22) Filed: Dec. 28, 2012

(51) Int. Cl.

| | |
|---|---|
| *A61K 31/765* | (2006.01) |
| *A61K 8/72* | (2006.01) |
| *A61K 8/18* | (2006.01) |
| *A61K 8/30* | (2006.01) |
| *A61K 31/341* | (2006.01) |
| *A61K 31/435* | (2006.01) |
| *A61Q 3/02* | (2006.01) |
| *A61Q 5/00* | (2006.01) |
| *A61Q 19/00* | (2006.01) |
| *C08F 2/00* | (2006.01) |
| *A61K 8/02* | (2006.01) |

(52) U.S. Cl.
USPC ............ 424/78.33; 424/70.1; 424/70.11; 424/70.17; 424/78.03; 424/401; 424/486; 514/277; 514/357; 514/461; 514/473; 526/204; 526/213; 526/216

(58) Field of Classification Search
USPC ............ 424/78.33, 70.1, 70.11, 70.17, 78.03, 424/401, 486; 514/277, 357, 461, 473; 526/204, 213, 216
See application file for complete search history.

(56) References Cited

U.S. PATENT DOCUMENTS

2013/0167859 A1* 7/2013 Bui et al. ................ 132/202

OTHER PUBLICATIONS

Wehrens et al., "Synthesis of a new photocrosslinkable prepolymer, based on poly(styrene-co-maleic anhydride)," Reactive & Functional Polymers, vol. 29, 1996, (pp. 21-27).

* cited by examiner

*Primary Examiner* — Jane C Oswecki
(74) *Attorney, Agent, or Firm* — The Marbury Law Group, PLLC

(57) ABSTRACT

Disclosed herein are cosmetic compositions comprising (a) at least one styrene-maleic anhydride copolymer bearing at least one group chosen from styrylpyridine and styrylpyridinium groups and (b) at least one co-film forming agent and/or at least one plasticizer. The cosmetic composition optionally further comprises at least one pigment and at least one solvent. Also disclosed herein are methods for making up and/or enhancing the appearance of a keratinous substrate comprising (1) forming a film on the keratinous substrate by applying to said keratinous substrate a cosmetic composition comprising (a) at least one styrene-maleic anhydride copolymer bearing at least one group chosen from styrylpyridine and styrylpyridinium groups and (b) at least one co-film forming agent and/or at least one plasticizer and (2) exposing the film to radiation chosen from UV and visible light radiation.

20 Claims, No Drawings

PHOTO-CURABLE RESIN FOR COSMETIC APPLICATION

FIELD OF THE DISCLOSURE

The disclosure relates to cosmetic compositions, such as nail compositions, comprising at least one photosensitive polymer resin. In various embodiments, the photosensitive polymer resin may comprise at least one reactive styrylpyridine or stytylpyridinium group. For example, the photosensitive polymer may be chosen from styrene-maleic anhydride copolymers bearing at least one styrylpyridine or styrylpyridinium group. Compositions according to the disclosure further comprise at least one co-film forming agent and/or at least one plasticizer. The compositions may optionally comprise at least one volatile solvent and/or at least one pigment.

In certain embodiments, the cosmetic compositions according to the disclosure do not require use of photoinitiators and can be cured by visible light and/or UV light. The compositions according to various embodiments may exhibit one or more improved properties, such as improved shine, adhesion, strength, flexibility, and/or long wear. Methods for making up keratinous substrates by applying the cosmetic compositions according to various embodiments of the disclosure to the substrates are also described herein.

BACKGROUND

Gel-based cosmetic compositions are known. For example, gel-based nail polishes have become increasingly popular in recent years, as they may provide improved properties over conventional nail polishes, such as extended wear and improved shine. However, consumers have raised safety concerns regarding the small molecules, such as the presence of photoinitiators and monomers in available gel-based nail polishes. In addition, gel-based nail polishes must be cured using UV radiation and can be difficult to remove. Furthermore, the application of gel-based nail polishes is expensive, time-consuming, and requires salon services for application and removal.

Thus, there is a desire in the cosmetic industry to provide consumers with safer and/or more convenient photo-curable cosmetic products that do not comprise small molecules such as photoinitiators, do not require curing with UV radiation, and/or exhibit improved ease of application and/or removal. In addition, it is desired that such photo-curable cosmetic products exhibit improved properties such as improved shine, gloss, adhesion, strength, flexibility, and/or long wear. As such, there is a continuous need to invent novel cosmetic compositions and methods of making up keratinous fibers which demonstrate one or more of said improved properties.

DESCRIPTION OF EXEMPLARY EMBODIMENTS

SMA-SBQ Polymers

The disclosure relates, in various embodiments, to cosmetic compositions comprising at least one photosensitive polymer resin. For example, the cosmetic composition may comprise at least one styrene-maleic anhydride copolymer based photosensitive resin. According to various embodiments of the disclosure, the photosensitive polymer resin bears reactive styrylpyridine or styrylpyridinium groups. In at least certain embodiments, the photosensitive resin may be chosen from styrene-maleic anhydride copolymers, such as those bearing at least one styrylpyridine group ("SMA-SBQ"). SMA-SBQ polymers are known in various arts as photocrosslinkable materials and are described, for example, in WEHRENS & TOMASCHEWSKI, "Synthesis of a new photocrosslinkable prepolymer, based on poly(styrene-co-maleic anhydride)," *Reactive & Functional Polymers*, vol. 29, pp. 21-27 (1996), incorporated herein by reference in its entirety.

Upon exposure to UV or visible light radiation, SMA-SBQ polymers are capable of crosslinking via a 2+2 cycloaddition reaction without the use of a photoinitiator. However, the use of SMA-SBQ polymers in the cosmetic arts is not known or described. It has now been surprisingly discovered that by incorporating at least one SMA-SBQ polymer into cosmetic compositions, optionally in combination with a co-film forming agent and/or plasticizer, a cosmetic film may be obtained which exhibits one or more improved cosmetic properties such as improved shine, gloss, adhesion, flexibility, strength, and/or long wear.

According to various exemplary embodiments of the disclosure, SMA-SBQ polymers may be chosen from copolymers obtained by reacting a styrene maleic anhydride ("SMA") copolymer with an amino functionalized styrylpyridine or styrylpyridinium ("SBQ") compound. For instance, suitable SMA-SBQ polymers may optionally be synthesized by the following reaction:

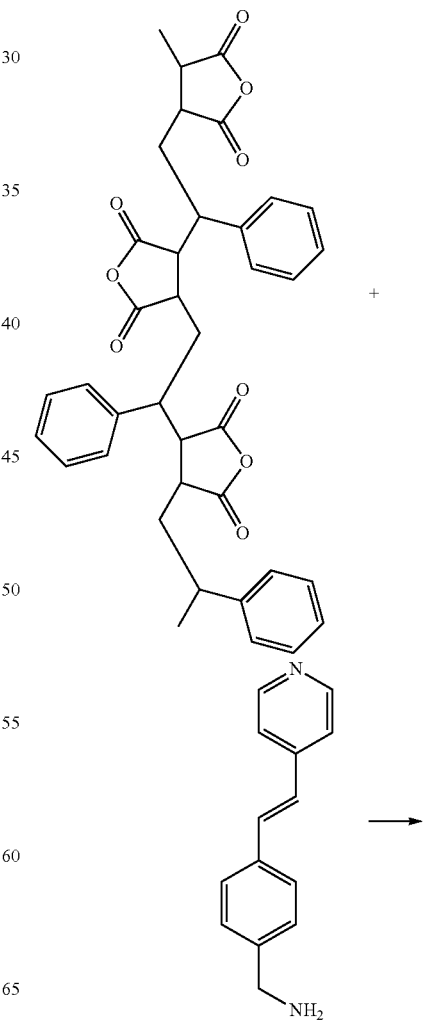

-continued

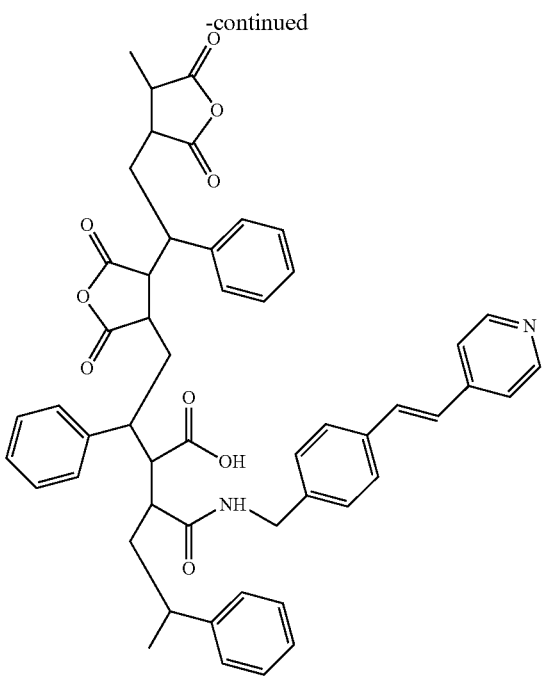

By way of non-limiting example, SMA copolymers may include the commercial products sold by Sartomer under the names SMA® 2021 (Mw approx 21,000) and SMA® 2000 (Mw approx. 7,500). In various exemplary embodiments, the molar ratio of SMA:SBQ in the at least one SMA-SBQ polymer may range from about 99.5:0.5 to about 80:20, such as, for example, about 99:1 to about 90:10, or about 98:2 to about 91:9. According to further exemplary embodiments, the at least one SMA-SBQ polymer may have a molecular weight ranging from about 1,000 to about 1,000,000, such as, for example, about 50,000 to about 500,000, or about 10,000 to about 100,000. In yet further exemplary embodiments, the at least one SMA-SBQ may have a degree of polymerization ranging from about 10 to about 10,000, for instance, from about 500 to about 5,000, or from about 100 to about 1,000.

According to various exemplary embodiments of the disclosure, the at least one SMA-SBQ polymer may be capable of crosslinking without the requirement of a photoinitiator. For example, without wishing to be bound, it is believed to be capable of crosslinking via a 2+2 cycloaddition reaction, upon exposure to UV or visible light radiation. For example, the at least one SMA-SBQ is capable of crosslinking without a photoinitiator upon exposure to radiation having a wavelength ranging from about 200 nm to about 800 nm, such as from about 250 nm to about 500 nm, or from about 265 nm to about 400 nm. In at least one exemplary embodiment, the at least one SMA-SBQ polymer is able to crosslink upon exposure to UV light radiation having a wavelength ranging from about 200 nm to about 400 nm. According to further exemplary embodiments, the at least one SMA-SBQ polymer is able to crosslink upon exposure to visible light radiation having a wavelength ranging from about 400 nm to about 800 nm.

In at least one exemplary embodiment, the at least one SMA-SBQ polymer may be present in the cosmetic composition in an amount ranging from about 5% to about 60% by weight, such as from about 10% to about 50%. According to another non-limiting embodiment, the at least one SMA-SBQ polymer may be present in the cosmetic composition in an amount ranging from about 15% to about 40% by weight.

Co-Film Forming Agents

As described herein, the cosmetic compositions comprising at least one photosensitive polymer resin, such as SMA-SBQ polymer, may also comprise at least one co-film forming agent. As used herein, the terms "film former," "film forming agent," "co-film forming agent," and variations thereof are understood to mean a polymer capable of forming, alone or in the presence of at least one additional agent which is able to form a film, an isolable film, for instance, a continuous and adherent film, on a keratinous substrate.

For example, depending on the application, SMA-SBQ resins may be more brittle than other film forming resins known in the art. In certain embodiments, the brittleness of the SMA-SBQ resins may be decreased by combining them with at least one co-film forming agent. In this way, the SMA-SBQ resins may be incorporated into cosmetic compositions, such as nail polish compositions, having improved long wear, adhesion, and gloss.

For instance, in certain embodiments, the at least one photosensitive polymer resin, such as SMA-SBQ resin, may be combined with at least one epoxy resin. Epoxy resins may provide good adhesion and may be less brittle and/or more flexible than the photosensitive polymer resin of the instant disclosure. In particular, the epoxy resins may have a glass transition temperature (Tg) of less than about 100° C., or less than about 80° C. Non-limiting examples of suitable epoxy resins include tosylamide epoxy resins, such as those sold by Estron Chemical under the tradename Polytex™, e.g., E-75, E-100, and NX-55. According to various exemplary embodiments, the composition may comprises a combination of at least SMA-SBQ polymer, at least one epoxy resin, and at least one additional co-film former, such as radical polymers, polycondensates, and polymers of natural origin.

Other examples of suitable co-film forming agents include, but are not limited to, meth(acrylic) resins; (meth)acrylic (co)polymers; styrene resins; acrylate-styrene resins; vinyl resins; vinyl polymers, such as polyvinylbutyral; vinyl copolymers; polyurethanes; polyesters; alkyd resins; cellulose polymers, such as nitrocellulose; cellulose esters, such as cellulose acetate, cellulose acetate propionate, and cellulose acetate butyrate; resins resulting from the condensation of formaldehyde with an arylsulphonamide; and mixtures thereof. It is also possible and within the scope of the instant disclosure to utilize one or more co-film formers exhibiting increased compatibility with water, such as starches and derivatives thereof, natural or synthetic gums and derivatives thereof, and water-soluble adhesives. According to at least one embodiment, the at least one co-film forming agent is chosen from resin film forming agents, for example, polyester and (meth)acrylic resins.

Suitable polyester resins include, but are not limited to, polyester resins formed by reacting a polyhydric alcohol with a polybasic acid, e.g., phthalic acid, such as the commercial product sold by Unitex Chemical Corporation under the name UNIPLEX 670-P, which is a polyester resin obtained by reacting trimellitic acid, neopentyl glycol, and adipic acid. (Meth)acrylic resins according to the disclosure may include copolymers of methyl methacrylate with butyl acrylate, butyl methacrylate, isobutyl methacrylate, or isobornyl methacrylate, for example, the commercial products PARALOID DM-55, PARALOID B48N, PARALOID B66, and ELVACITE 2550; copolymers of isobutylmethacrylate and butyl methacrylate, for instance, the commercial product ELVACITE 2046; and isobutyl methacrylate polymers, for example, PARALOID B67.

In accordance with various exemplary embodiments, the at least one co-film forming agent may be present in the cosmetic composition in an amount ranging from about 5% to about 50% by weight, such as from about 10% to about 30%, or from about 15% to about 20%, relative to the total weight of the cosmetic composition.

Plasticizers

The cosmetic compositions of the disclosure may also comprise at least one plasticizer. Any conventional plasticizing agent known in the cosmetic art, such as, for example, those known to be useful in nail polish compositions, can be used. For example, suitable plasticizers may be chosen from glycols and their ether and ester derivatives; esters of acids, for example, esters of carboxylic acids such as citrates, adipates, carbonates, tartrates, phosphates, and sebacates; oxyethylenated derivatives such as oxyethylenated oils; and mixtures thereof. Non-limiting examples of plasticizers useful in accordance with the instant disclosure include tributyl phosphate, tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl)acetylcitrate, dibutyl tartrate, camphor, and mixtures thereof.

In accordance with various embodiments, the plasticizer may be present in the composition in an amount ranging from about 0.01% to about 25% by weight, such as from about 0.1% to about 22% by weight, or from about 1 to about 20% by weight, relative to the total weight of the cosmetic composition.

Pigments

At least one pigment may optionally be added to the compositions of the disclosure to provide cosmetically acceptable shades and/or to opacify the films. The pigments can be organic or inorganic. Non-limiting examples of suitable pigments include red pigments, for example, D & C red Nos. 10, 11, 12 and 13, D & C red No. 7, and TOB-BON maroon (D & C red No. 34). Other pigments which may be used in compositions according to the present disclosure include the Lake pigments, for example, D & C yellow No. 5 Lake, D & C Red No. 2 Lake, and Ext. D & C Red No. 2 Lake. Additional pigments other than the pigments listed above can include cosmetic-grade or purified titanium dioxide (white), yellow and red iron oxides, iron blue, iron black, ultramarine blue, chromide oxide greens, carbon black or lampblack. Such additional pigments may be present in minute quantities. Iridescent additives may also be included, for example, "pearl essence," which is a suspension of crystalline guanine in nitrocellulose and solvents, as well as other additives which may affect the appearance of the pigment.

The amount of pigment in the cosmetic compositions of the present disclosure will vary as a function of the type of pigment and other components included in the compositions. However, in general, the pigments are included in a total amount ranging from about 0.025% to about 10% by weight, for example, from about 0.5% to about 4% by weight of the composition.

Solvents

The cosmetic compositions of the disclosure may further comprise at least one solvent, such as, for example, those chosen from volatile solvents. Any conventional solvent known in the cosmetic art, such as those known to be useful in nail polish compositions, can be used. For instance, suitable solvents may include organic solvents which are liquid at ambient temperature. By way of non-limiting example, the cosmetic composition may include at least one volatile solvent chosen from ketones such as methyl ethyl ketone, methyl isobutyl ketone, diisobutyl ketone, isophorone, cyclohexanone, and acetone; alcohols, such as ethanol, isopropanol, diacetone alcohol, 2-butoxyethanol, and cyclohexanol; glycols, such as ethylene glycol, propylene glycol, pentylene glycol, and glycerol; propylene glycol ethers, such as propylene glycol monomethyl ether, propylene glycol monomethyl ether acetate, and dipropylene glycol mono (n-butyl)ether; short-chain esters (comprising from 2 to 8 carbon atoms), such as ethyl acetate, methyl acetate, propyl acetate, n-butyl acetate, and isopentyl acetate; alkanes, such as decane, heptane, dodecane, and cyclohexane; aldehydes, such as benzaldehyde and acetaldehyde; and mixtures thereof. According to various exemplary embodiments, the at least one solvent is chosen from short-chain esters.

The at least one solvent may be present in the cosmetic composition in any suitable amount, such as, for example, an amount ranging from about 1% to about 90% by weight, such as from about 10% to about 80% by weight, or from about 30 to about 75% by weight, relative to the total weight of the composition.

Additives

Additives and auxiliary agents commonly known in the cosmetic arts may be included in the compositions of the instant disclosure. For instance, additives known to be useful in the formulation of nail polish compositions may be included in the compositions of the present disclosure. Exemplary additives include, but are not limited to, thickeners, coalescents, preservatives, fragrances, oils, waxes, surfactants, antioxidants, agents for combating free radicals, spreading agents, wetting agents, dispersing agents, antifoaming agents, neutralizing agents, stabilizing agents, active principles chosen from essential oils, UV screening agents, sunscreens, moisturizing agents, vitamins, proteins, ceramides, plant extracts, fibers, and mixtures thereof.

A person skilled in the art will take care to select the optional additional additives and/or the amounts thereof such that the advantageous properties of the composition according to the invention are not, or are not substantially, adversely affected by the envisaged addition. These substances may be selected variously by the person skilled in the art in order to prepare a composition which has the desired properties, for example, good adhesion or longer wear.

Needless to say, the composition of the invention should be cosmetically and dermatologically acceptable, i.e., it should contain non-toxic physiologically acceptable components. The composition may be in any form normally employed in the cosmetic and dermatological fields and suitable for topical application to a keratinous substrate. Exemplary cosmetic compositions contemplated according to the disclosure include compositions intended for application to keratinous substrates, such as the hair, skin, and nails. Such compositions include, but are not limited to, nail compositions (e.g. nail enamel), mascara compositions, make-up compositions (e.g. foundations), sunscreen compositions, and hair-care compositions (e.g. hair-styling compositions). In at least one exemplary and non-limiting embodiment, the cosmetic composition is a nail polish composition.

One exemplary and non-limiting embodiment of the disclosure relates to cosmetic compositions comprising (1) at least one SMA-SBQ polymer and (2) at least one co-film forming agent chosen from epoxy resins.

A further exemplary and non-limiting embodiment of the disclosure relates to cosmetic compositions comprising (1) at least one SMA-SBQ polymer and (2) at least one plasticizer.

Another exemplary and non-limiting embodiment of the disclosure relates to cosmetic compositions comprising (1) at least one SMA-SBQ polymer, (2) at least one co-film forming agent chosen from epoxy resins, and (3) at least one plasticizer.

Methods

Also disclosed herein are methods for making up and/or enhancing the appearance of a keratinous substrate comprising (1) forming a film on said keratinous substrate by applying to the keratinous substrate a cosmetic composition comprising (a) at least one SMA-SBQ polymer and (b) at least one co-film forming agent and/or at least one plasticizer and (2) exposing the film to radiation chosen from UV and visible light radiation. In certain embodiments, the at least one co-film forming agent is an epoxy resin. The compositions may further comprise at least one pigment and/or at least one volatile solvent.

According to various non-limiting methods disclosed herein, the film formed on the keratinous substrate may be subsequently exposed to radiation chosen from UV and visible light radiation. In at least one exemplary embodiment, the film is exposed to radiation having a wavelength ranging from about 200 nm to about 800 nm. By way of non-limiting example, the film may be exposed to UV radiation having a wavelength ranging from about 200 nm to about 400 nm and/or visible light radiation having a wavelength ranging from about 400 nm to about 800 nm. The film may, in other embodiments, be exposed to radiation having a wavelength ranging from about 250 nm to about 500 nm, for example, from about 265 nm to about 400 nm.

In various exemplary embodiments, the film may be exposed to radiation for a time period ranging from about 0.5 minutes to about 60 minutes, for example, from about 1 minute to about 30 minutes, or from about 2 minutes to about 10 minutes.

It is to be understood that both the foregoing description and the following Examples are exemplary and explanatory only, and are not to be interpreted as restrictive of the disclosure. Moreover, it should be understood that various features and/or characteristics of differing embodiments herein may be combined with one another. It is therefore to be understood that numerous modifications may be made to the illustrative embodiments and that other arrangements may be devised without departing from the scope of the invention. Other embodiments will be apparent to those skilled in the art from consideration of the disclosure and practice of the various exemplary embodiments disclosed herein.

It is also to be understood that, as used herein the terms "the," "a," or "an," mean "at least one," and should not be limited to "only one" unless explicitly indicated to the contrary. Thus, for example, the use of "a SMA-SBQ polymer" is intended to mean at least one SMA-SBQ polymer.

Unless otherwise indicated, all numbers used in the specification and claims are to be understood as being modified in all instances by the term "about," whether or not so stated. It should also be understood that the precise numerical values used in the specification and claims form additional embodiments of the invention, and are intended to include any ranges which can be narrowed to any two end points disclosed within the exemplary ranges and values provided. Efforts have been made to ensure the accuracy of the numerical values disclosed herein. Any measured numerical value, however, can inherently contain certain errors resulting from the standard deviation found in its respective measuring technique.

EXAMPLES

The following Examples are intended to be non-restrictive and explanatory only, with the scope of the invention being defined by the claims.

Example 1

Clear Nail Enamels

Three simple clear nail enamel compositions were prepared by mixing the components listed in the following Table I. All values are listed as percentages by weight.

TABLE I

Preparation of Clear Nail Enamels

| Composition | SMA-SBQ[1] | Tosylamide Epoxy Resin[2] | Tributyl Citrate[3] | Ethyl Acetate | Curing Method |
|---|---|---|---|---|---|
| 1 | 25% | — | — | 75% | Gelish harmony 18 G LED lamp, 6 min or suntester with UV filter, 10 min |
| 2 | 18.75% | 18.75% | — | 62.5% | Gelish harmony 18 G LED lamp, 6 min |
| 3 | 16.7% | 16.7% | 10.7% | 55.9% | Gelish harmony 18 G LED lamp, 6 min |

[1]SMA ® 2021 (Mw = 21,000) reacted with amino functionalized styrylpyridine, bearing 8.6 mol % styrylpyridine groups
[2]POLYTEX ™ NX-55
[3]UNIPLEX 83

Each of compositions 1-3 was applied on to a polymethyl methacrylate (PMMA) plate using a drawndown bar to produce a wet coating approximately 75 μm thick. The coatings were then cured using either a Gelish harmony 18G LED lamp or sun tester with UV filter (cured with visible light). After curing, the glass transition temperatures of the films were measured by differential scanning calorimetry (DSC). The glass transition measurements are provided in Table II below.

TABLE II

Glass Transition Temperatures

| COMPOSITION | $T_g$ (° C.) |
|---|---|
| 1 | 181 |
| 2 | 48.5 |
| 3 | −20.4 |

It was noted that Composition 1, comprising only SMA-SBQ resin, was very brittle and incapable of forming a film. Composition 2, comprising SMA-SBQ and a co-film forming agent (epoxy resin) was less brittle and able to form a film. Composition 3, comprising PVA-SBQ, epoxy resin, and a plasticizer formed a very flexible film. Thus, by incorporating an epoxy resin and/or a plasticizer into a composition comprising SMA-SBQ, a less brittle and more flexible film can be obtained.

What is claimed is:
1. A cosmetic composition comprising:
(a) at least one styrene-maleic anhydride (SMA) copolymer bearing at least one group (SBQ) chosen from styrylpyridine and styrylpyridinium groups; and

(b) at least one co-film forming agent and/or at least one plasticizer.

2. The cosmetic composition of claim 1, wherein the ratio of SMA:SBQ in the at least one SMA copolymer bearing at least one SBQ group ranges from about 99:1 to about 80:20.

3. The cosmetic composition of claim 1, wherein the at least one SMA copolymer bearing at least one SBQ group is present in the cosmetic composition in an amount ranging from about 5% to about 40% by weight relative to the total weight of the composition.

4. The cosmetic composition of claim 1, further comprising at least one pigment and/or at least one solvent.

5. The cosmetic composition of claim 1 wherein the at least one co-film forming agent is chosen from epoxy resins, (meth)acrylic resins, (meth)acrylic (co)polymers, styrene resins, acrylate-styrene resins, vinyl resins, vinyl polymers, vinyl copolymers, polyurethanes, polyesters, alkyd resins, cellulose polymers, cellulose esters, resins resulting from the condensation of formaldehyde with an arylsulphonamide, and mixtures thereof.

6. The cosmetic composition of claim 5, wherein the at least one co-film forming agent is chosen from epoxy resins.

7. The cosmetic composition of claim 6, wherein the epoxy resins have a glass transition temperature of less than 100° C.

8. The cosmetic composition of claim 1, wherein the at least one co-film forming agent is present in the composition in an amount ranging from about 5% to about 30% by weight relative to the total weight of the composition.

9. The cosmetic composition of claim 1, wherein the at least one plasticizer is chosen from tributyl phosphate, tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl)acetylcitrate, dibutyl tartrate, camphor, and mixtures thereof.

10. The cosmetic composition of claim 1, wherein the at least one plasticizer is present in the composition in an amount ranging from about 0.01% to about 25% by weight, relative to the total weight of the cosmetic composition.

11. The cosmetic composition of claim 4, wherein the at least one pigment is present in the composition in an amount ranging from about 0.025% to about 10% by weight, relative to the total weight of the cosmetic composition.

12. The cosmetic composition of claim 4, wherein the at least one solvent is chosen from ketones, alcohols, glycols, propylene glycol ethers, short-chain esters comprising from 2 to 8 carbon atoms, alkanes, aldehydes, and mixtures thereof.

13. The cosmetic composition of claim 4, wherein the at least one solvent is present in the composition in an amount ranging from about 1% to about 90% by weight, relative to the total weight of the cosmetic composition.

14. The cosmetic composition of claim 1, chosen from nail compositions, make-up compositions, mascara compositions, hair-care compositions, and sunscreen compositions.

15. A method of making up and/or enhancing the appearance of a keratinous substrate comprising:
(1) forming a film on the keratinous substrate by applying to said keratinous substrate a cosmetic composition comprising:
(a) at least one styrene-maleic anhydride (SMA) copolymer bearing at least one group (SBQ) chosen from styrylpyridine and styrylpyridinium groups, and
(b) at least one co-film forming agent and/or at least one plasticizer; and
(2) exposing the film to radiation chosen from UV and visible light radiation.

16. The method of claim 15, wherein the cosmetic composition further comprises at least one pigment and/or at least one solvent.

17. The method of claim 15, wherein the at least one co-film forming agent is chosen from epoxy resins.

18. The method of claim 15, wherein the at least one plasticizer is chosen from tributyl phosphate, tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl)acetylcitrate, dibutyl tartrate, camphor, and mixtures thereof.

19. The method of claim 15, wherein the film is exposed to radiation having a wavelength ranging from about 200 nm to about 800 nm.

20. The method of claim 15, wherein the film is exposed to radiation for a time period ranging from about 0.5 minutes to about 30 minutes.

\* \* \* \* \*